(12) United States Patent
Ichimura et al.

(10) Patent No.: US 10,631,719 B2
(45) Date of Patent: Apr. 28, 2020

(54) ENDOSCOPE

(71) Applicants: OLYMPUS CORPORATION, Tokyo (JP); PANASONIC CORPORATION, Osaka (JP)

(72) Inventors: Hironobu Ichimura, Akishima (JP); Tomohisa Takahashi, Hachioji (JP); Tomokazu Yamashita, Ibaraki (JP); Noriyuki Fujimori, Suwa (JP); Takatoshi Igarashi, Ina (JP); Yoshiki Takayama, Otsu (JP)

(73) Assignees: OLYMPUS CORPORATION, Tokyo (JP); PANASONIC CORPORATION, Osaka (JP)

( * ) Notice: Subject to any disclaimer, the term of this patent is extended or adjusted under 35 U.S.C. 154(b) by 362 days.

(21) Appl. No.: 15/613,399

(22) Filed: Jun. 5, 2017

(65) Prior Publication Data
US 2017/0265721 A1 Sep. 21, 2017

Related U.S. Application Data

(63) Continuation of application No. PCT/JP2015/081194, filed on Nov. 5, 2015.

(30) Foreign Application Priority Data

Dec. 9, 2014 (JP) .................................. 2014-249356

(51) Int. Cl.
*A61B 1/05* (2006.01)
*A61B 1/04* (2006.01)
(Continued)

(52) U.S. Cl.
CPC .......... *A61B 1/051* (2013.01); *A61B 1/00096* (2013.01); *A61B 1/04* (2013.01);
(Continued)

(58) Field of Classification Search
CPC ... A61B 1/00096; A61B 1/00124; A61B 1/05; A61B 1/051
See application file for complete search history.

(56) References Cited

U.S. PATENT DOCUMENTS 4,741,327 A * 5/1988 Yabe .................. A61B 1/00177
348/65
5,427,087 A 6/1995 Ito et al.
(Continued)

FOREIGN PATENT DOCUMENTS

JP H04-193253 A 7/1992
JP H09-307087 A 11/1997
(Continued)

OTHER PUBLICATIONS

International Search Report dated Jan. 26, 2016 issued in PCT/JP2015/081194.
(Continued)

*Primary Examiner* — Aaron B Fairchild
(74) *Attorney, Agent, or Firm* — Scully, Scott, Murphy & Presser, P.C.

(57) ABSTRACT

An endoscope includes: an imaging unit disposed at a distal end portion of an insertion section inserted into a body of a subject; and a built-in component provided parallel with the imaging unit at the distal end portion, and extending substantially parallel with an axial direction of the insertion section. The imaging unit includes: a solid state image sensor including a light receiving unit; a flexible circuit board electrically connecting the solid state image sensor; and a rigid circuit board at least partially disposed on a proximal end side of the endoscope relative to the solid state image sensor, and electrically connected to the flexible circuit board.

4 Claims, 13 Drawing Sheets

(51) Int. Cl.
*A61B 1/00* (2006.01)
*H04N 5/225* (2006.01)
*G02B 23/24* (2006.01)

(52) U.S. Cl.
CPC ............... *A61B 1/0011* (2013.01); *A61B 1/05* (2013.01); *G02B 23/2476* (2013.01); *G02B 23/2484* (2013.01); *H04N 5/2253* (2013.01); *H04N 2005/2255* (2013.01)

(56) References Cited

U.S. PATENT DOCUMENTS

| | | | |
|---|---|---|---|
| 5,454,366 A | 10/1995 | Ito et al. | |
| 8,679,000 B2* | 3/2014 | Kimura | A61B 1/051 600/110 |
| 9,345,395 B2* | 5/2016 | Takahashi | A61B 1/00096 |
| 2002/0080233 A1* | 6/2002 | Irion | H04N 5/2251 348/65 |
| 2007/0162095 A1* | 7/2007 | Kimmel | A61B 1/00089 600/109 |
| 2011/0313252 A1* | 12/2011 | Lin | A61B 1/0008 600/162 |
| 2012/0220825 A1* | 8/2012 | Kimura | A61B 1/051 600/109 |
| 2015/0190039 A1* | 7/2015 | Takahashi | A61B 1/00096 600/109 |
| 2016/0028926 A1* | 1/2016 | Ichimura | A61B 1/051 348/68 |
| 2016/0205296 A1* | 7/2016 | Igarashi | A61B 1/0008 348/76 |
| 2016/0206186 A1* | 7/2016 | Igarashi | A61B 1/0008 |
| 2017/0255001 A1* | 9/2017 | Yamashita | A61B 1/0011 |

FOREIGN PATENT DOCUMENTS

| | | |
|---|---|---|
| JP | 2000-125161 A | 4/2000 |
| JP | 2009-136609 A | 6/2009 |
| JP | 2012-147968 A | 8/2012 |
| JP | 5166012 | 3/2013 |
| JP | 2013-179981 A | 9/2013 |

OTHER PUBLICATIONS

Extended Supplementary European Search Report dated Aug. 29, 2018 in European Patent Application No. 15 86 8292.2.

* cited by examiner

FIG.13
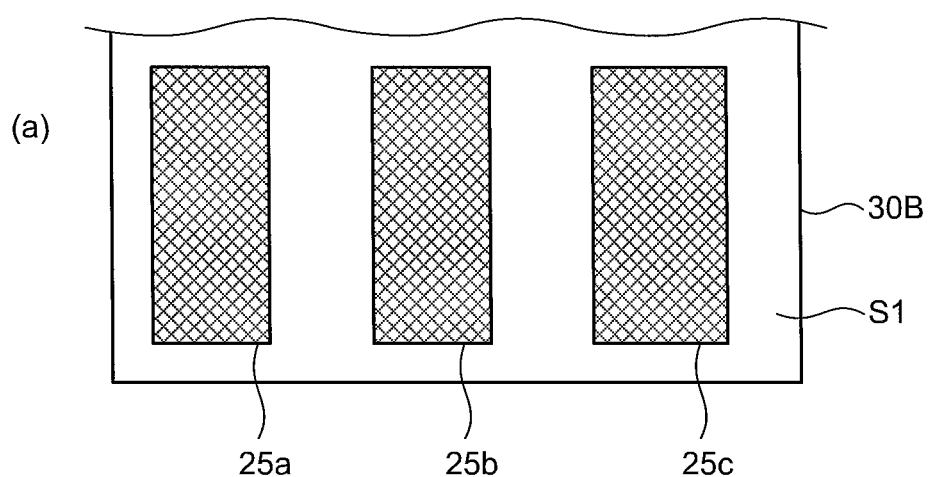
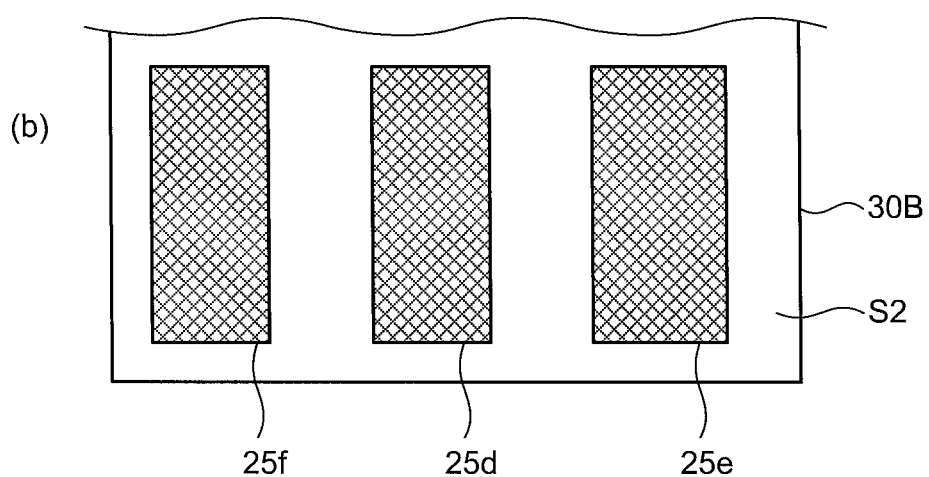

FIG.14
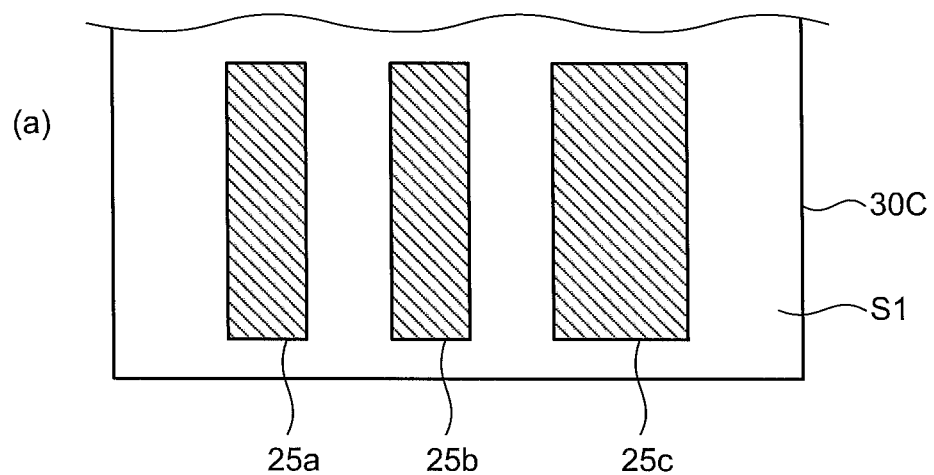
(a)
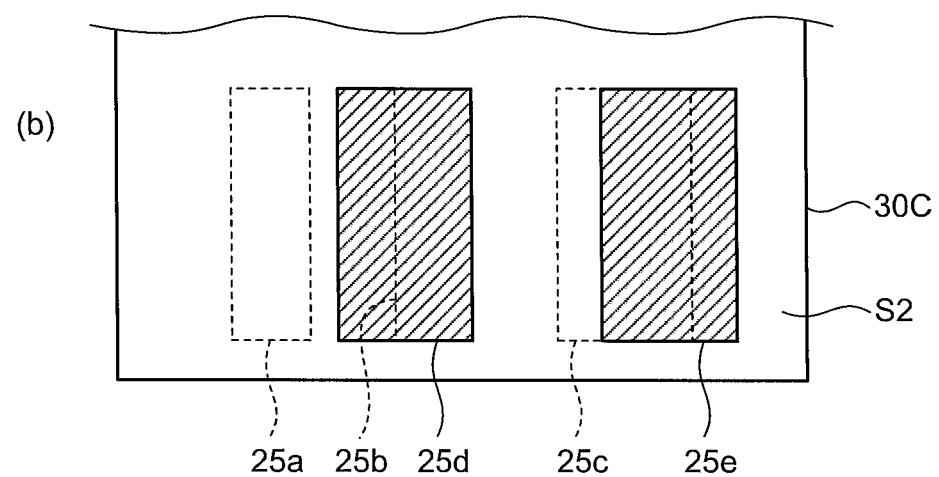
(b)

ENDOSCOPE

CROSS-REFERENCE TO RELATED APPLICATIONS

This application is a continuation of PCT international application Ser. No. PCT/JP2015/081194 filed on Nov. 5, 2015 which designates the United States, incorporated herein by reference, and which claims the benefit of priority from Japanese Patent Applications No. 2014-249356, filed on Dec. 9, 2014, incorporated herein by reference.

BACKGROUND

The present disclosure relates to an endoscope.

In a medical field and an industrial field, endoscopes are widely used for various inspections. Endoscopes for medical use have a flexible elongated insertion section having a distal end provided with a solid state image sensor, and the insertion section is inserted into a subject such as a patient to acquire an in-vivo image in a body cavity of the subject without incision, and further to treat the subject using a treatment instrument projecting from the distal end of the insertion section if necessary. Thus, the endoscopes have been widely used.

In such an endoscope, a diameter of the insertion section is required to be reduced. As a technique to reduce a size of the insertion section, an imaging device is provided in which a circuit board having an image sensor mounted thereon, and a signal cable connected thereto includes a plurality of layers, a minor axis of the circuit board and a radius of the endoscope are disposed to be parallel in direction, and the layered circuit board has a width reduced toward an outer periphery of the endoscope to have a stepped form. Such an imaging device preventing interference with a case at the distal end of the endoscope, and reducing the diameter of the endoscope is disclosed (e.g., see JP 2012-147968 A).

There is a need for an endoscope achieving reduction in diameter of an insertion section storing an imaging device and a built-in component.

SUMMARY

An endoscope according to one aspect of the present disclosure includes: an imaging unit disposed at a distal end portion of an insertion section inserted into a body of a subject; and a built-in component provided parallel with the imaging unit at the distal end portion, and extending substantially parallel with an axial direction of the insertion section, wherein the imaging unit includes: a solid state image sensor including a light receiving unit; and a flexible circuit board electrically connecting the solid state image sensor; a rigid circuit board at least partially disposed on a proximal end side of the endoscope relative to the solid state image sensor, and electrically connected to the flexible circuit board, the rigid circuit board includes a first surface whose longitudinal direction extends in an axial direction of the distal end portion, and a second surface opposed to the first surface substantially in parallel, the first surface having a width larger than a width of the second surface in a cross-section orthogonal to the longitudinal direction, the rigid circuit board includes a third surface and a fourth surface different from the first surface and the second surface, and the third surface and the fourth surface extending in an axial direction of the distal end portion, and the third surface or the fourth surface being opposed to the built-in component, the solid state image sensor includes a light receiving surface provided with the light receiving unit, a land on the sensor for connection with the flexible circuit board is formed on the light receiving surface, and the light receiving surface is disposed orthogonal to the axial direction of the distal end portion, the rigid circuit board is formed with a land on the circuit board for connection with the flexible circuit board, on the first or second surface, and is disposed such that a fifth surface orthogonal to the axial direction of the distal end portion is opposed to a surface opposite to the light receiving surface of the solid state image sensor, and the flexible circuit board is disposed to be opposed to a side surface of the light receiving surface of the solid state image sensor, and the first or second surface of the rigid circuit board.

An endoscope according to another aspect of the present disclosure includes: an imaging unit disposed at a distal end portion of an insertion section inserted into a body of a subject; and a built-in component provided parallel with the imaging unit at the distal end portion, and extending substantially parallel with an axial direction of the insertion section, wherein the imaging unit includes: a solid state image sensor including a light receiving unit; and a rigid circuit board at least partially disposed on a proximal end side of the endoscope relative to the solid state image sensor, and electrically connected to the solid state image sensor, the rigid circuit board includes a first surface whose longitudinal direction extends in an axial direction of the distal end portion, and a second surface opposed to the first surface substantially in parallel, the first surface having a width larger than a width of the second surface in a cross-section orthogonal to the longitudinal direction, the rigid circuit board includes a third surface and a fourth surface different from the first surface and the second surface, and the third surface and the fourth surface extending in an axial direction of the distal end portion, and the third surface or the fourth surface being opposed to the built-in component, the solid state image sensor includes a light receiving surface provided with the light receiving unit, a land on the sensor for connection with the rigid circuit board is formed on the light receiving surface, and the light receiving surface is disposed parallel with the axial direction of the distal end portion, the rigid circuit board is formed with a land on the circuit board for connection with the solid state image sensor, on the first or second surface, and is disposed so that the first or second surface is opposed to the light receiving surface of the solid state image sensor, and the solid state image sensor is mounted on the rigid circuit board so that the land on the sensor is connected to the land on the circuit board.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 13 is a top view and a bottom view of an end portion of a rigid circuit board of FIG. 11;

FIG. 14 is a top view and a bottom view of an end portion of a rigid circuit board conventionally used;

DETAILED DESCRIPTION

Figure 1:
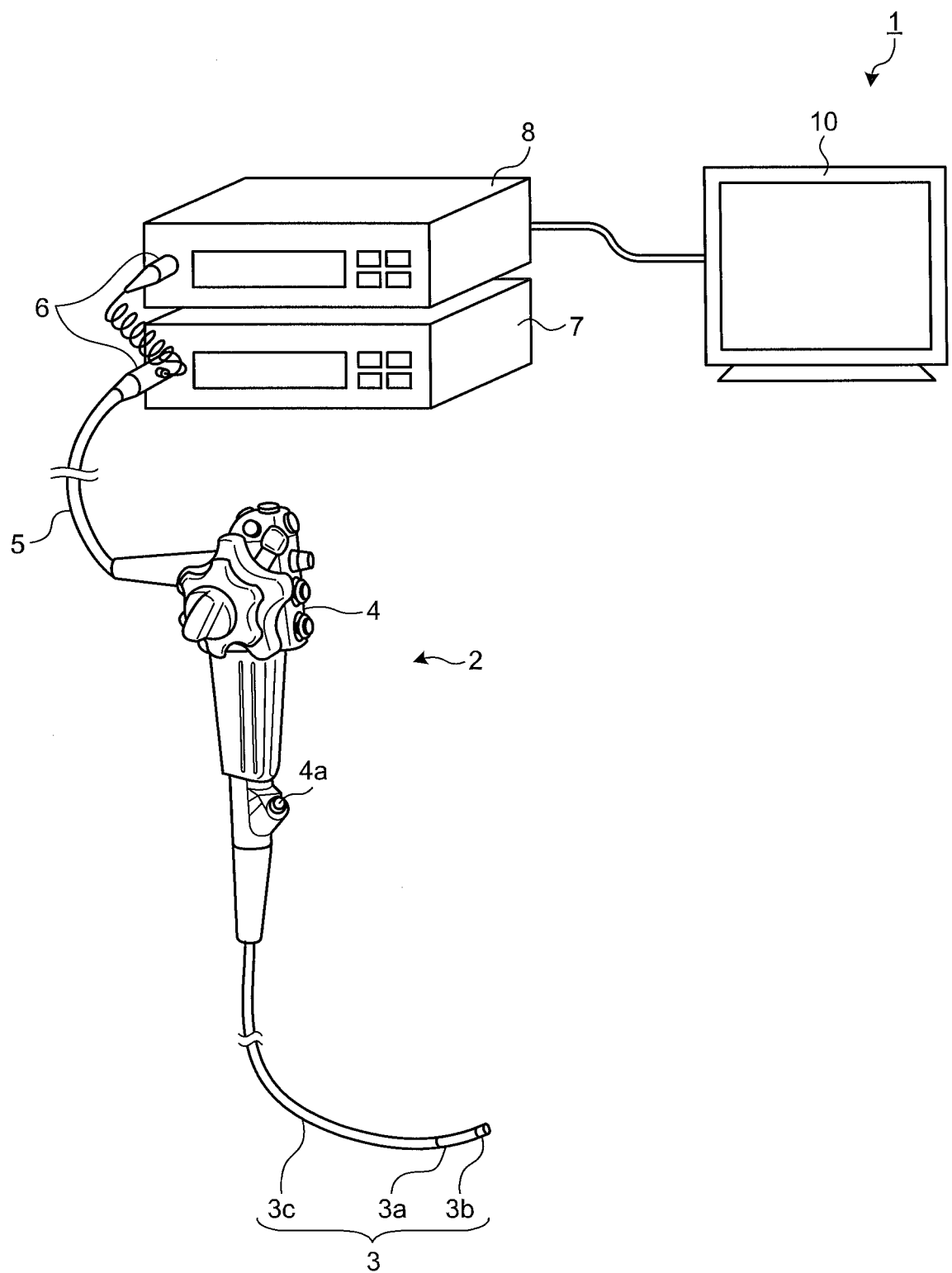
FIG. 1 is a schematic view of an overall configuration of an endoscope apparatus according to a first embodiment of the present disclosure.

An endoscope including an imaging unit will be described below as modes for carrying out the present disclosure (hereinafter, referred to as "embodiments"). The present disclosure is not limited to this embodiment. Further, in the drawings, the same portions are denoted by the same reference signs. Still furthermore, it should be noted that the drawings are schematically illustrated, and relationships between the thicknesses and the widths, the proportions, or the like of members may be different from those of actual ones. In addition, the drawings include portions which are different in size or proportion between the drawings.

First Embodiment

FIG. 1 is a schematic view of an overall configuration of an endoscope apparatus according to a first embodiment of the present disclosure. As illustrated in FIG. 1, an endoscope apparatus 1 includes an endoscope 2, a universal cord 5, a connector 6, a light source device 7, a processor (control device) 8, and a display device 10.

The endoscope 2 is configured to insert an insertion section 3 into a body cavity of a subject to capture an in-vivo image of the subject, and output an imaging signal. The universal cord 5 contains cables extending to a distal end of the insertion section 3 of the endoscope 2, and connected to an imaging unit provided at a distal end portion 3b of the insertion section 3.

The connector 6 is provided at a proximal end of the universal cord 5, is connected to the light source device 7 and the processor 8, performs predetermined signal processing on the imaging signal (output signal) output from the imaging unit at the distal end portion 3b connected to the universal cord 5, and performs analog-digital conversion (A/D conversion) on the imaging signal to output the imaging signal as an image signal.

The light source device 7, for example, includes a white LED. The light source device 7 emits pulsed white light, and the pulsed white light is emitted, as illumination light, from the distal end of the insertion section 3 of the endoscope 2 to an object through the connector 6 and the universal cord 5.

The processor 8 performs predetermined image processing on the image signal output from the connector 6, and controls the whole of the endoscope apparatus 1. The display device 10 displays the image signal processed by the processor 8.

The insertion section 3 of the endoscope 2 has a proximal end side on which an operating unit 4 is connected, and the operating unit 4 is provided with various buttons or knobs for operating the functions of the endoscope. The operating unit 4 is provided with a treatment instrument insertion opening 4a for inserting a treatment instrument such as biopsy forceps, an electrosurgical knife, or an inspection probe, into the body cavity of the subject.

The insertion section 3 includes the distal end portion 3b provided with the imaging unit, a bending section 3a connected to a proximal end side of the distal end portion 3b to be freely bent in a vertical direction, and a flexible tube portion 3c connected to a proximal end side of the bending section 3a. The bending section 3a is bent by operation of a bending operation knob provided at the operating unit 4, and, for example, freely bent in two directions, that is, upward and downward, with pulling and releasing of a bending wire inserted through the insertion section 3.

In the endoscope 2, a light guide 15 (FIG. 2) is disposed for transmitting illumination light from the light source device 7, and an illumination window is disposed at an emission end of the light guide 15 from which illumination light is emitted. This illumination window is provided at the distal end portion 3b of the insertion section 3 to emit illumination light to the subject.

Next, a configuration of the distal end portion 3b of the endoscope 2 will be described in detail. FIG. 2(a) is a front view of a distal end of the endoscope 2, and FIG. 2(b) is a partial cross-sectional view of the distal end of the endoscope 2. The partial cross-sectional view of FIG. 2(b) is a cross-sectional view taken along a plane parallel with a surface of a circuit board of the imaging unit provided at the distal end portion 3b of the endoscope 2, and parallel with an optical axis direction of the imaging unit. FIG. 2(b) illustrates the distal end portion 3b of the insertion section 3 of the endoscope 2.

Figure 2:
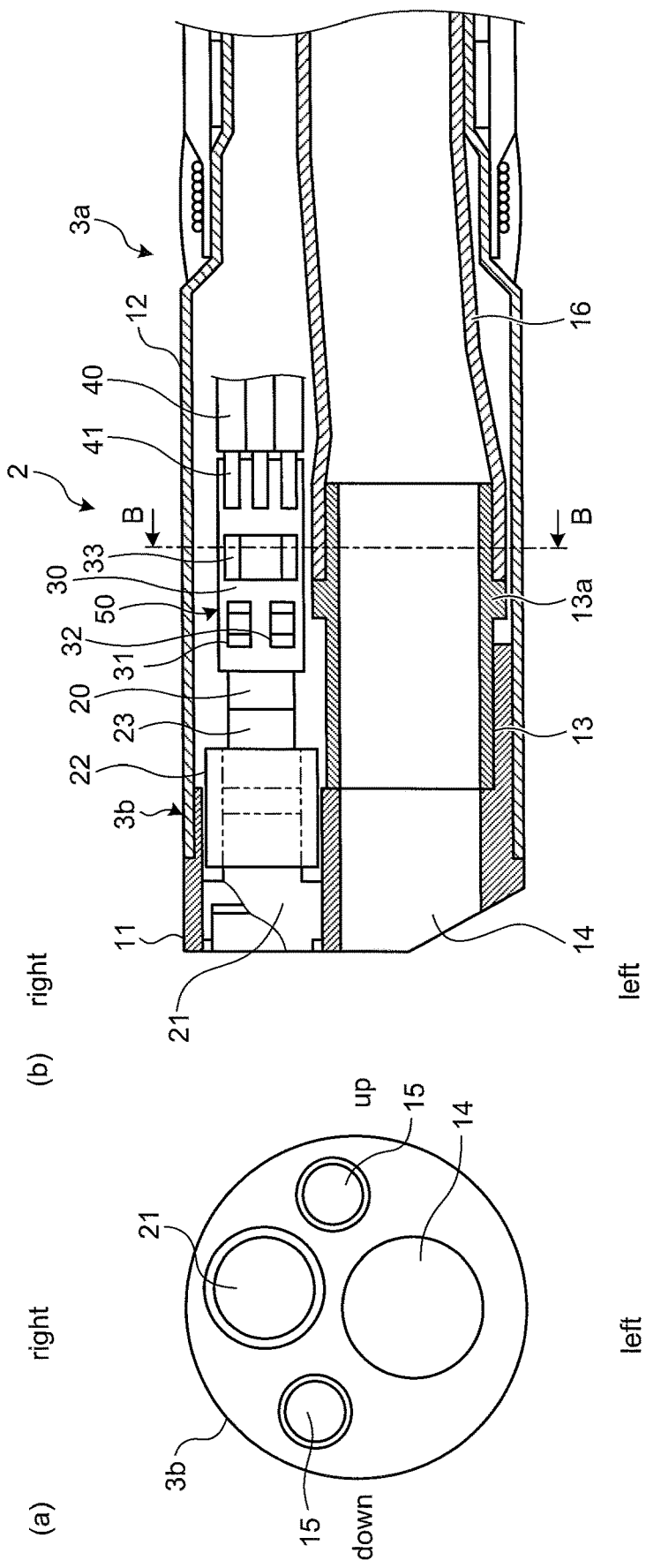
FIG. 2 is a front view and a partial cross-sectional view of a distal end of an endoscope illustrated in FIG. 1.

As illustrated in FIG. 2, the distal end portion 3b of the insertion section 3 of the endoscope 2 stores an imaging unit 50, a forceps channel 14 for inserting a treatment instrument such as forceps, an electrosurgical knife, or an inspection probe, and two light guides 15 for transmitting illumination light. According to the present first embodiment, the imaging unit 50 is disposed on the right side, the forceps channel 14 on the left side, and the light guides 15 on the upper side and lower side. In the present description, members other than the imaging unit 50 stored in the distal end portion 3*b* provided parallel with the imaging unit 50 in the distal end portion 3*b*, and extending substantially parallel with an axial direction of the insertion section 3, such as the forceps channel 14 and the light guide 15, correspond to the built-in components.

The bending section 3*a* may be freely bent in the vertical direction, with the pulling and releasing of the bending wire passing into a bending tube disposed inside a sheath tube 12. The imaging unit 50 is provided in the distal end portion 3*b* extending toward a distal end of the bending section 3*a*. The sheath tube 12 includes a flexible member so that the bending section 3*a* may be bent.

The forceps channel 14 includes a metal pipe 13 positioned with respect to a distal end body 11, and a tube 16 having a distal end covering a proximal end of the metal pipe 13, and the other end extending to the treatment instrument insertion opening 4*a*. The tube 16 has a distal end portion abutting on a flange portion 13*a* provided on an outer periphery of the metal pipe 13.

The imaging unit 50 has a lens unit 21, and a solid state image sensor 20 disposed on a proximal end side of the lens unit 21, and is bonded inside the distal end body 11 with an adhesive. The distal end body 11 includes a rigid member forming an internal space for storing the imaging unit 50.

The lens unit 21 includes a plurality of objective lenses (not illustrated), the lens unit 21 has a doublet lens 21*a* bonded to a cover glass described later (see FIG. 3), and a lens holder 22 holding the objective lens and the doublet lens 21*a*, the lens holder 22 has a distal end fixedly inserted into the distal end body 11, and the lens unit 21 is fixed to the distal end.

The imaging unit 50 has the solid state image sensor 20, such as a CCD or a CMOS, having a light receiving unit 20*a* for receiving light, a flexible circuit board 38 (see FIG. 3) extending from the solid state image sensor 20, a rigid circuit board 30 on which electronic components 31 to 36 constituting a drive circuit of the solid state image sensor 20 are mounted, a cover glass 23 bonded to the solid state image sensor 20 while covering the light receiving unit 20*a* of the solid state image sensor 20, and a plurality of signal cables 40 supplying power to the solid state image sensor 20, or inputting and outputting signals to and from the solid state image sensor 20.

Each of the signal cables 40 has a core wire 41 connected to a cable land provided on the rigid circuit board 30, and the signal cable 40 has a proximal end extending toward the proximal end of the insertion section 3. The signal cable 40 extends to the connector 6, through the operating unit 4 and the universal cord 5 illustrated in FIG. 1.

An Image of the subject formed by the lens unit 21 is detected by the solid state image sensor 20 disposed at an imaging point of the lens unit 21, and is converted into the imaging signal. The imaging signal (output signal) is output to the processor 8, through the flexible circuit board 38, the rigid circuit board 30, and the signal cable 40.

Figure 3:
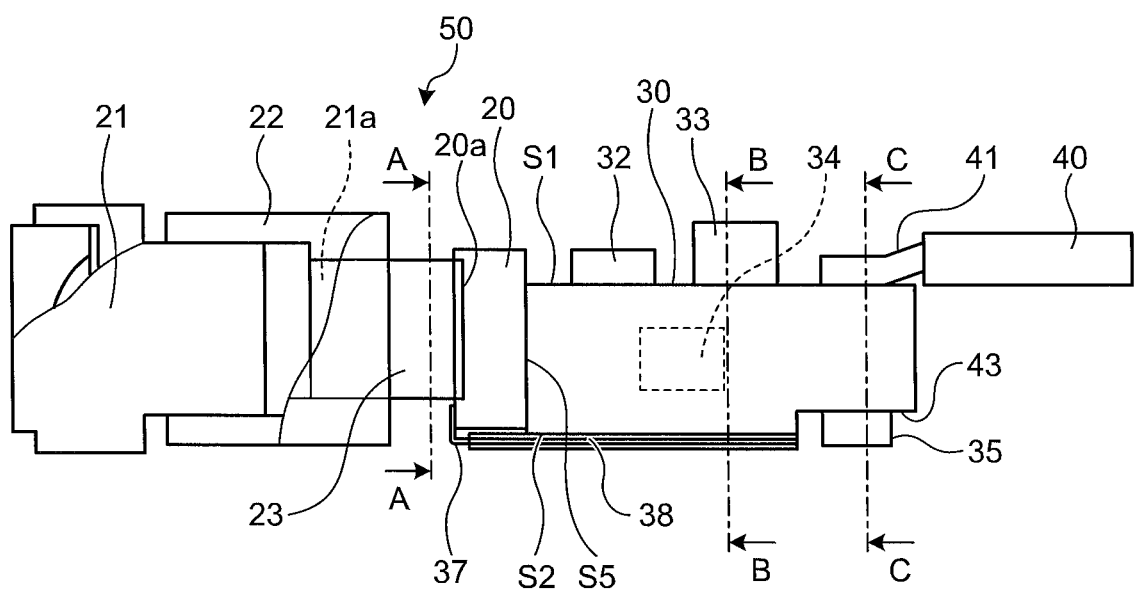
FIG. 3 is a left side view of an imaging device included in the endoscope illustrated in FIG. 1.
Figure 4:
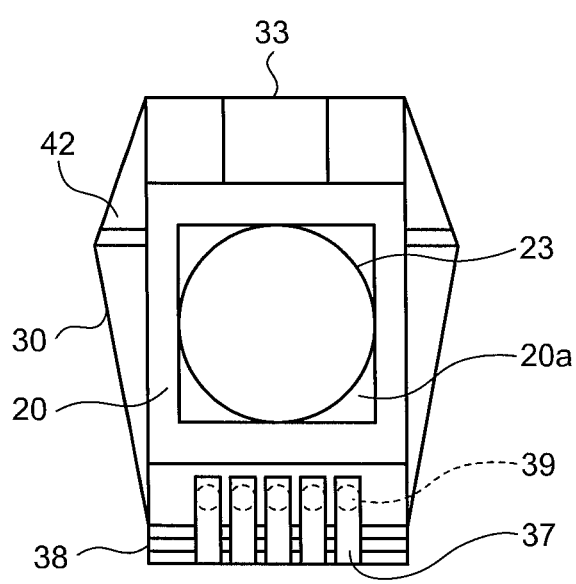
FIG. 4 is a cross-sectional view taken along a line A-A of FIG. 3.
Figure 5:
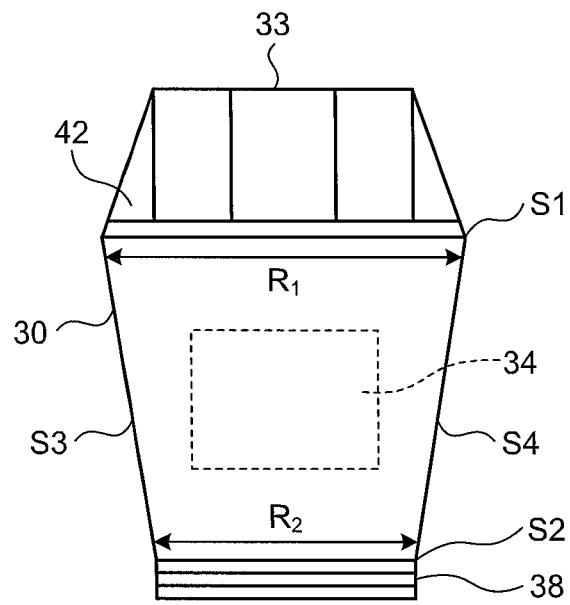
FIG. 5 is a cross-sectional view taken along a line B-B of FIG. 3.
Figure 6:
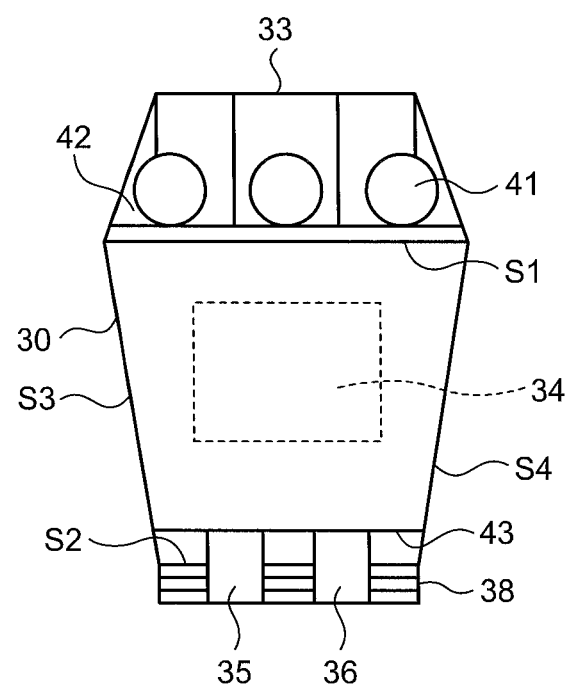
FIG. 6 is a cross-sectional view taken along a line C-C of FIG. 3.
Figure 7:
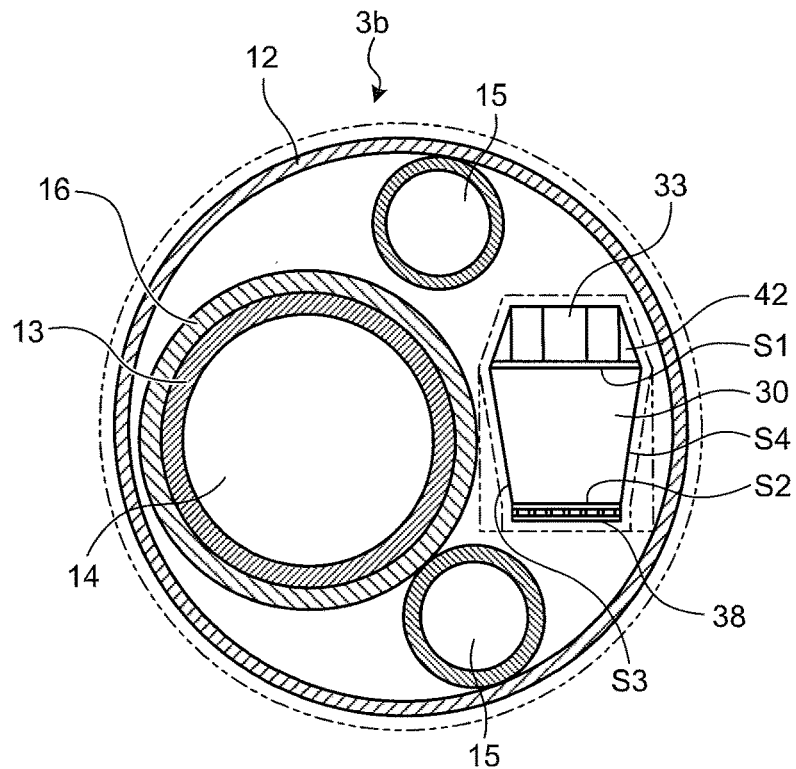
FIG. 7 is a cross-sectional view taken along a line B-B of FIG. 2.

Next, the imaging unit 50 will be described. FIG. 3 is a left side view of the imaging unit 50 included in the endoscope 2 illustrated in FIG. 1. FIG. 4 is a cross-sectional view taken along a line A-A of FIG. 3. FIG. 5 is a cross-sectional view taken along a line B-B of FIG. 3. FIG. 6 is a cross-sectional view taken along a line C-C of FIG. 3. FIG. 7 is a cross-sectional view of the distal end portion 3*b* of the endoscope 2 which is taken along a line B-B of FIG. 2.

As illustrated in FIGS. 3 and 4, a light receiving surface of the solid state image sensor 20 is provided with the light receiving unit 20*a*, and the light receiving surface is provided with lands on the sensor, and inner leads 37 of the flexible circuit board 38 are electrically and mechanically connected to the lands through bumps 39. The flexible circuit board 38 is a flexible printed circuit board, and extends in a lateral direction from the light receiving surface of the solid state image sensor 20 on which the light receiving unit 20*a* is provided.

The rigid circuit board 30 is disposed behind the solid state image sensor 20, that is, on a proximal end side of the distal end portion 3*b*, and is electrically connected to the solid state image sensor 20 through the flexible circuit board 38. The rigid circuit board 30 has a first surface S1 having a longitudinal direction extending in an axial direction of the distal end portion 3*b*, that is, in the optical axis direction of the imaging unit 50, and a second surface S2 parallel with the first surface S1. As illustrated in FIGS. 5 and 6, in cross-sections orthogonal to the longitudinal direction of the rigid circuit board 30 (cross sectional views taken along the line B-B and the line C-C of FIG. 3), the first surface S1 has a width $R_1$ formed larger than a width $R_2$ of the second surface S2. In the present first embodiment, the other surfaces different from the first surface S1 and the second surface S2, and having a longitudinal direction extending in the axial direction of the distal end portion 3*b*, that is, a third surface S3 and a fourth surface S4, form a tapered shape from the first surface S1 to the second surface S2. The tapered shape between the third surface S3 and the fourth surface S4 may be formed by obliquely cutting with a dicing blade.

A wiring pattern such as electronic component mounting lands for mounting the electronic components 31, 32, and 33, and the cable lands for connecting the signal cables 40 are disposed, on the first surface S1 of the rigid circuit board 30. On the second surface S2, a step portion 43 for mounting the electronic components 35 and 36 is formed on a proximal end side. Furthermore, on the second surface S2, electronic component mounting lands for mounting the electronic components 35 and 36, and lands on the circuit board for electrically and mechanically connecting the flexible circuit board 38 are disposed. In the rigid circuit board 30, the wiring pattern including vias, electronic component mounting lands, and the like is disposed, and the electronic component 34 is incorporated. The flexible circuit board 38 is disposed from the light receiving surface to a side surface of the solid state image sensor 20, opposing the second surface S2 of the rigid circuit board 30. Note that the lands on the circuit board of the rigid circuit board 30 may be disposed on the first surface S1 so that the flexible circuit board 38 is disposed opposing the first surface S1 of the rigid circuit board 30.

The electronic components 31 to 36 are mounted to the electronic component mounting lands through solder 42. The electronic component 33 of the electronic components 31 to 36 has the longest major axis, and the electronic component 33 is preferably mounted orthogonal to the longitudinal direction of the rigid circuit board 30, that is, orthogonal to the optical axis direction. Mounting of the electronic component 33 to have the longest major axis orthogonal to the longitudinal direction of the rigid circuit board 30 reduces a longitudinal length of the rigid circuit board 30 and further reduce a length of the distal end portion 3*b*. Furthermore, the electronic component 33 having the highest mounting height of the electronic components 31 to 36 is preferably mounted on the first surface S1. The rigid circuit board 30 may include a ceramic substrate, in addition to a resin substrate, especially a laminated resin substrate having a multiple layers of a thermoplastic resin.

The rigid circuit board 30 abuts on a surface orthogonal to the longitudinal direction of the rigid circuit board 30, that is, a fifth surface S5 orthogonal to the optical axis direction of the imaging unit 50, and positioned on a side of the solid state image sensor 20, opposite to the light receiving surface. The rigid circuit board 30 and the solid state image sensor 20 are preferably fixed with a thermosetting resin adhesive.

In the rigid circuit board 30, the third surface S3 or the fourth surface S4 being a surface different from the first surface S1 and the second surface S2, and extending in the axial direction of the distal end portion 3b are disposed to be adjacently opposed to the forceps channel 14 or the light guide 15 being the built-in component in the distal end portion 3b. The imaging unit 50 is disposed so that the built-in component and the third surface S3 or the fourth surface S4 formed into the tapered shape are adjacently opposed to each other, and the diameter of the distal end portion 3b may be reduced as described below.

The third surface S3 or the fourth surface S4 being a surface different from the first surface S1 and the second surface S2, and extending in the axial direction of the distal end portion 3b is preferably adjacently opposed to a built-in component having the largest diameter of the built-in components stored in the distal end portion 3b. As illustrated in FIG. 7, in the present first embodiment, the third surface S3 is adjacently opposed to the built-in component having the largest diameter, that is, the forceps channel 14, and the fourth surface S4 is adjacently opposed to the sheath tube 12.

Figure 8:
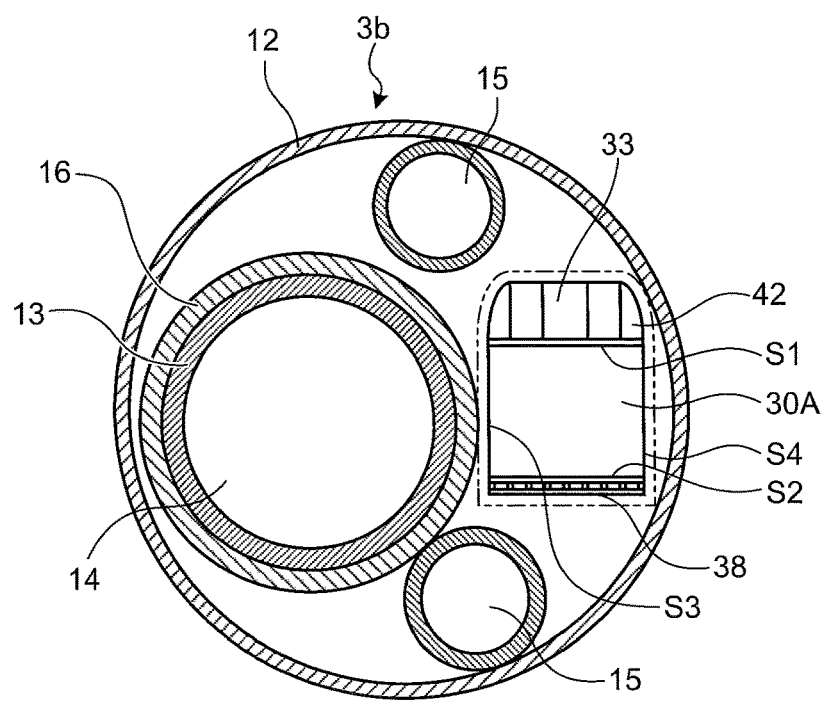
FIG. 8 is a cross-sectional view of a distal end of a conventional endoscope.
Figure 9:
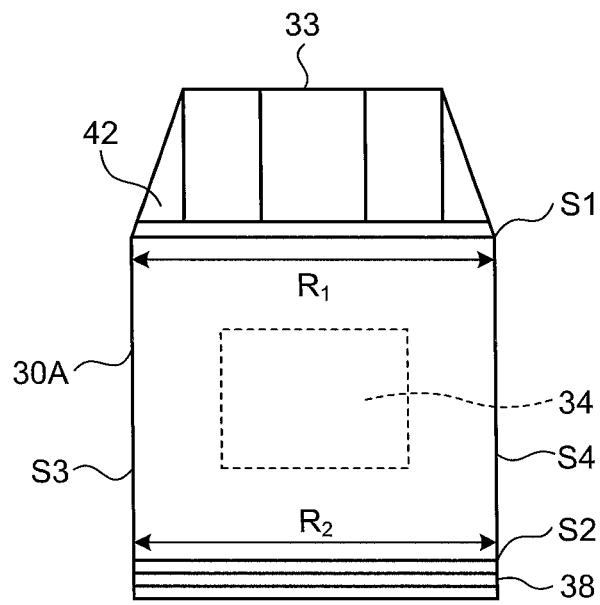
FIG. 9 is a cross-sectional view of a conventional imaging unit using a rigid circuit board.
Figure 10:
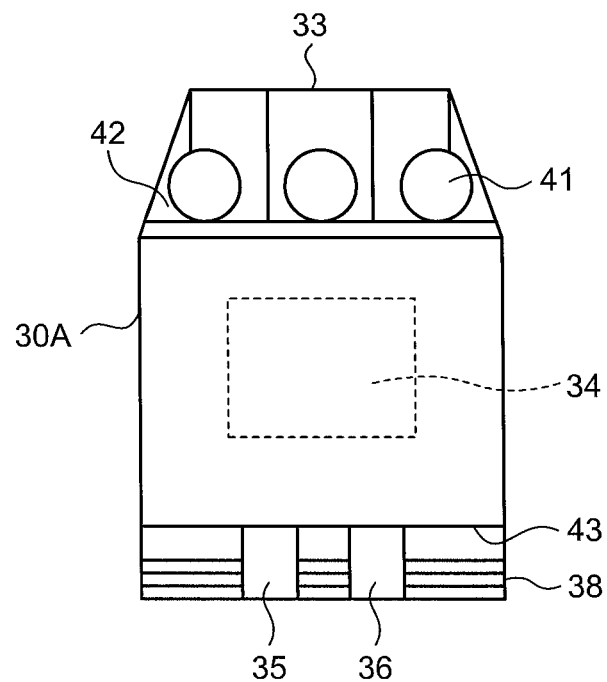
FIG. 10 is a cross-sectional view of the conventional imaging unit using the rigid circuit board.

FIG. 8 is a cross-sectional view of a distal end of a conventional endoscope (cross-sectional view taken at the same position as the line B-B of FIG. 2). FIG. 9 is a cross-sectional view of a conventional imaging unit using a rigid circuit board (cross-sectional view taken at the same position as the line B-B of FIG. 3). FIG. 10 is a cross-sectional view of the conventional imaging unit using the rigid circuit board (cross-sectional view taken at the same position as the line C-C of FIG. 3). As illustrated in FIGS. 9 and 10, in a rigid circuit board 30A used in a conventional imaging device, the width $R_1$ of the first surface S1 is equal to the width $R_2$ of the second surface S2, and thus, when the third surface S3 is adjacently opposed to the forceps channel 14, and the fourth surface S4 is adjacently opposed to the sheath tube 12, an outer diameter of the distal end portion 3b is increased, as illustrated in FIG. 8

In FIG. 7, a maximum external shape of the imaging unit 50 is indicated by a one dot chain line, and a maximum external shape of the conventional imaging device is indicated by a two-dot chain line, around the rigid circuit board 30, In FIG. 8, a maximum external shape of the conventional imaging device using the rigid circuit board 30A is indicated by a two-dot chain line, around the rigid circuit board 30A conventionally used. As illustrated in FIG. 7, in the conventional imaging device having the maximum external shape indicated by the two-dot chain line, the third surface S3 and the fourth surface S4 do not form a tapered shape. Thus, in order to avoid interference between the forceps channel 14 and the sheath tube 12, the outer diameter of the distal end portion 3b needs to be increased up to a size indicated by the two-dot chain line, around the sheath tube 12.

According to the first embodiment, the third surface S3 and the fourth surface S4 of the rigid circuit board 30 form the tapered shape, the width $R_1$ of the first surface S1 in the cross-section orthogonal to the longitudinal direction is increased relative to the width $R_2$ of the second surface S2, the rigid circuit board 30 is disposed so that the third surface S3 is adjacently opposed to the forceps channel 14 as the built-in component, and the fourth surface S4 is adjacently opposed to the sheath tube 12, and the diameter of the distal end portion 3b may be reduced.

Note that, in the present first embodiment, the third surface S3 and the fourth surface S4 form the tapered shape, but only one of the third surface S3 and the fourth surface S4 may form a tapered shape to be opposed to the built-in component.

According to the first embodiment, the forceps channel 14 and the endoscope 2 storing the two light guides 15 have been described, but also in an endoscope having only one light guide as the built-in component, or in an endoscope or the like having an air/water channel as the built-in component, in addition to the forceps channel, the third surface S3 or the fourth surface S4 forming a tapered shape is adjacently opposed to the built-in component, preferably the built-in component having the largest diameter to reduce the diameter of the distal end portion 3b.

In the present first embodiment, the width $R_1$ of the first surface S1 is formed larger than the width $R_2$ of the second surface S2, but when the rigid circuit board 30 is disposed below the forceps channel 14, the width $R_1$ of the first surface S1 may be formed smaller than the width $R_2$ of the second surface S2, and the third surface S3 and the fourth surface S4 may form an inverted tapered shape to reduce the diameter of the distal end portion 3b.

Figure 11:
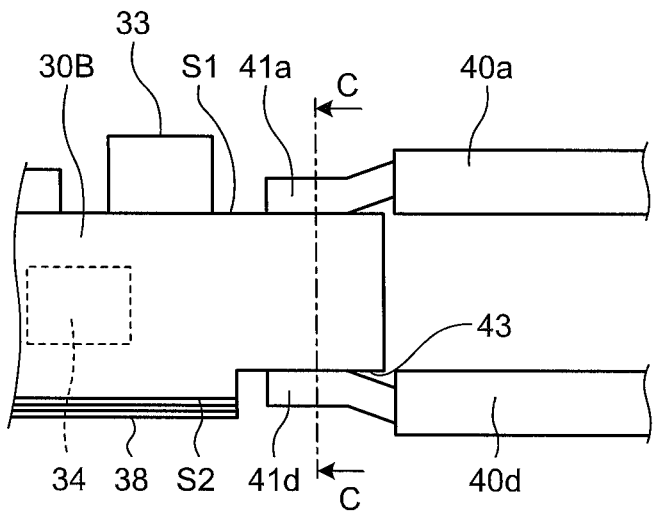
FIG. 11 is a partial side view of an imaging unit according to a modification of the first embodiment of the present disclosure.
Figure 12:
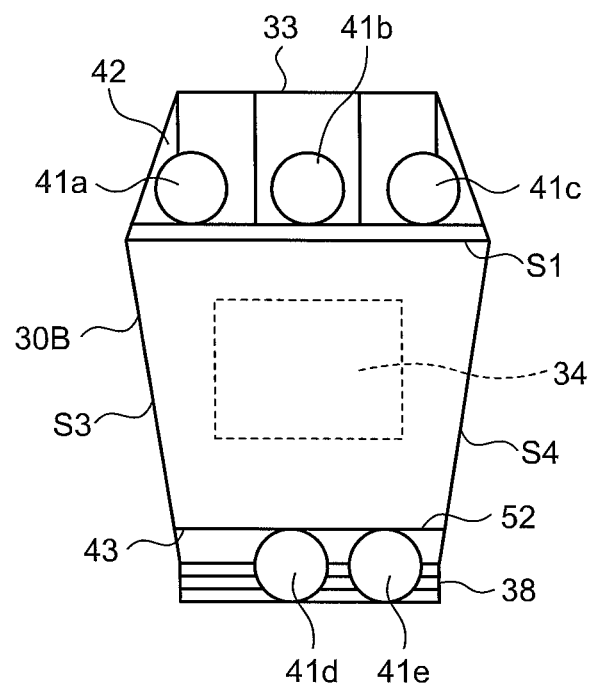
FIG. 12 is a cross-sectional view taken along a line C-C of FIG. 11.

Furthermore, to the step portion 43 formed on the second surface S2 of the rigid circuit board 30, not the electronic components but the signal cables may be connected. FIG. 11 is a partial side view of an imaging unit according to a modification of the first embodiment of the present disclosure. FIG. 12 is a cross-sectional view taken along a line C-C of FIG. 11. FIG. 13(a) is a perspective view of a proximal end portion of the first surface S1 of the rigid circuit board of FIG. 11, and FIG. 13(b) is a perspective view of the second surface S2 (step portion 43) of the rigid circuit board of FIG. 11, which is viewed from a side of the first surface S1. FIG. 14 (a) is a perspective view of the proximal end portion of the first surface S1 of a rigid circuit board conventionally used, and FIG. 14 (b) is a perspective view of the second surface S2 (step portion 43) of the rigid circuit board conventionally used, which is viewed from a side of the first surface S1.

In the modification of the first embodiment, signal cables 40a to 40c are connected to the proximal end portion, in a longitudinal direction, of the first surface S1 of a rigid circuit board 30B, and signal cables 40d and 40e are connected to the step portion 43 of the second surface S2.

As illustrated in FIG. 13, cable lands 25a to 25c connecting core wires 41a to 41c of the signal cables 40a to 40c, respectively, are provided, on the first surface S1 of the rigid circuit board 30B. Furthermore, the second surface S2 is provided with cable lands 25d and 25e connecting core wires 41d and 41e of the signal cables 40d and 40e, and a test land 25f is provided.

The signal cables 40a to 40c connected to the first surface S1, and the signal cable 40e connected to the second surface S2 are cables for transmitting drive signals of the electronic components, and the signal cable 40d connected to the second surface S2 is a cable for an output signal.

In order to connect five signal cables 40a to 40e to a rigid circuit board 30C, the first surface S1 of the proximal end portion of the rigid circuit board 30C is provided with the cable lands 25a to 25c connecting the signal cables 40a to 40c, and the second surface S2 is provided with the cable lands 25d and 25e connecting the signal cables 40d and 40e, as illustrated in FIG. 14.

Commonly, for examination of connection between the flexible circuit board 38 and the solid state image sensor 20, and examination of electrical characteristics upon connection between the flexible circuit board 38 and the rigid circuit board 30C, a terminal of an inspection device is brought into contact with the cable lands 25a to 25e, and examination of the electrical characteristics is performed. The examination is performed by bringing examination terminals into pressure-contact with the cable lands 25a to 25e, respectively, from above and below the rigid circuit board 30C, but in the rigid circuit board 30C conventionally used, the first surface S1 and the second surface S2 have a different number of or different arrangement of the cable lands, and it is difficult to ensure contact of all the examination terminals with the cable lands.

In the present modification, the second surface S2 is provided with the test land 25f for examination of a signal input from the solid state image sensor 20 to an electronic component, and the arrangement positions of the cable lands are formed at the same positions on the first surface S1 and the second surface S2, and when the examination terminals are brought into contact with the cable lands, a rotation moment does not occur, and the examination terminals may be reliably brought into contact with the cable lands. Furthermore, a signal input from the solid state image sensor 20 to an electronic component may be examined by the test land 25f, and failure of an electronic component may be examined.

Second Embodiment

Figure 15:
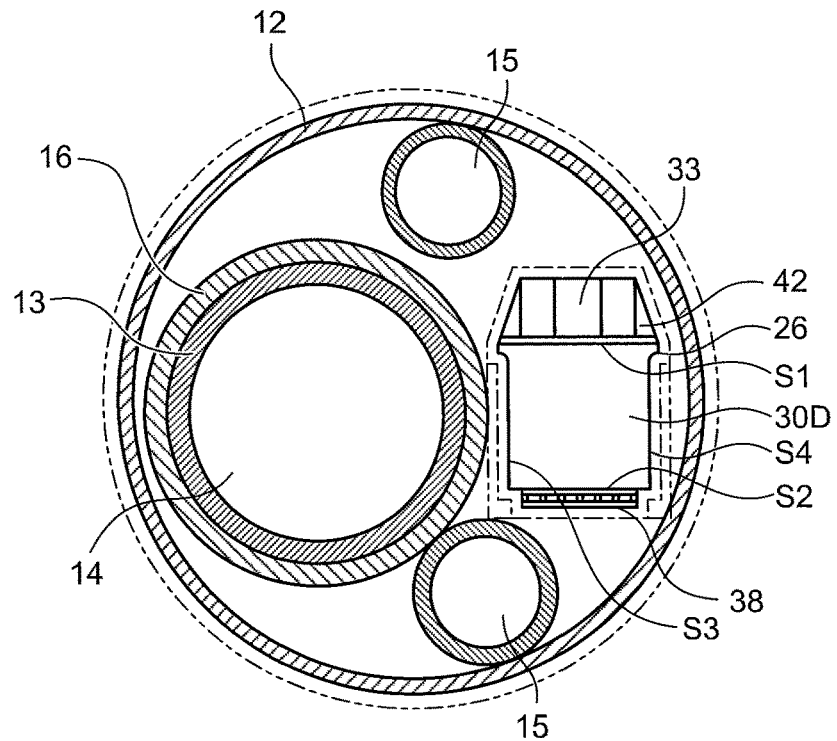
FIG. 15 is a cross-sectional view of a distal end of an endoscope according to a second embodiment of the present disclosure.

FIG. 15 is a cross-sectional view of a distal end of an endoscope according to a second embodiment of the present disclosure. The cross-sectional view illustrated in FIG. 15 is taken at the same position as the B-B line of FIG. 2. In FIG. 15, a maximum external shape of an imaging device according to the second embodiment is indicated by a one-dot chain line, and a maximum external shape of the conventional imaging device is indicated by a two-dot chain line, around a rigid circuit board 30D. In the endoscope according to the second embodiment, a rounded portion (curved surface portion) 26 is provided on the third surface S3 and the fourth surface S4 of the rigid circuit board 30D. The other configuration is similar to that of the first embodiment.

Usually, the rigid circuit board 30D is formed such that a plurality of electronic components is mounted on a collective substrate including a plurality of rigid circuit boards, and then, the collective substrate is cut into individual rigid circuit boards 30D with a dicing blade or the like. After the collective substrate is cut with the dicing blade, the rounded portion (curved surface portion) 26 is generated in the cutout. According to the second embodiment, the rounded portion (curved surface portion) 26 is entirely left so that the electronic component 33 are mounted up to the rounded portion (curved surface portion) 26.

According to the second embodiment, the rounded portions (curved surface portion) 26 are entirely left on the third surface S3 and the fourth surface S4, and the width of the first surface S1 may be formed larger than the width of the second surface S2, in a cross-section orthogonal to a longitudinal direction of the rigid circuit board 30D. Since the third surface S3 is adjacently opposed to the forceps channel 14, interference between the rigid circuit board 30D, the forceps channel 14, and the sheath tube 12 are not generated, and the outer diameter of the distal end portion 3b may be reduced relative to that of the conventional one. Furthermore, according to the second embodiment, since a fillet of solder 42 is provided over the rounded portion (curved surface portion) 26, the chipping in dicing of the rigid circuit board 30D may be reduced.

Third Embodiment

Figure 16:
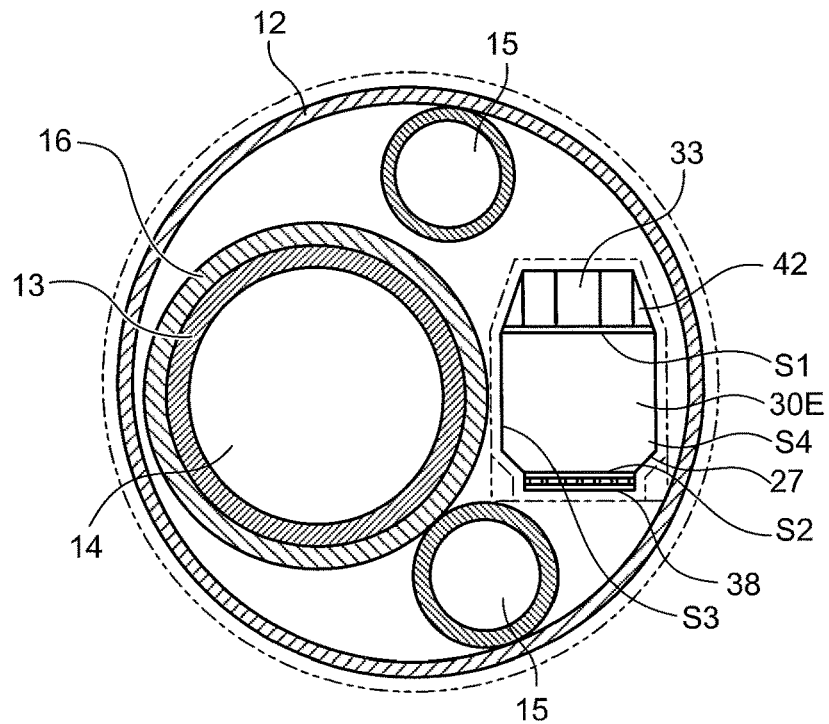
FIG. 16 is a cross-sectional view of a distal end of an endoscope according to a third embodiment of the present disclosure.

FIG. 16 is a cross-sectional view of a distal end of an endoscope according to a third embodiment of the present disclosure. The cross-sectional view illustrated in FIG. 16 is taken at the same position as the B-B line of FIG. 2. In FIG. 16, a maximum external shape of an imaging device according to the third embodiment is indicated by a one-dot chain line, and a maximum external shape of the conventional imaging device is indicated by a two-dot chain line, around a rigid circuit board 30E. In the endoscope according to the third embodiment, a chamfered portion 27 is provided on the third surface S3 and the fourth surface S4 of the rigid circuit board 30E. The other configuration is similar to that of the first embodiment.

After the rigid circuit board 30E according to the third embodiment is cut out into a rigid circuit board having a cuboid shape, the chamfered portions 27 are preferably formed at corners of the third surface S3 and the fourth surface S4, respectively.

According to the third embodiment, the chamfered portions 27 are provided on the third surface S3 and the fourth surface S4, and a length of the first surface S1 may be formed longer than a length of the second surface S2, in a cross-section orthogonal to a longitudinal direction of the rigid circuit board 30E. Since the third surface S3 is adjacently opposed to the forceps channel 14, interference between the rigid circuit board 30E, the forceps channel 14, and the sheath tube 12 are not generated, and the distal end portion may have an outer diameter smaller than that of the conventional one.

Fourth Embodiment

Figure 17:
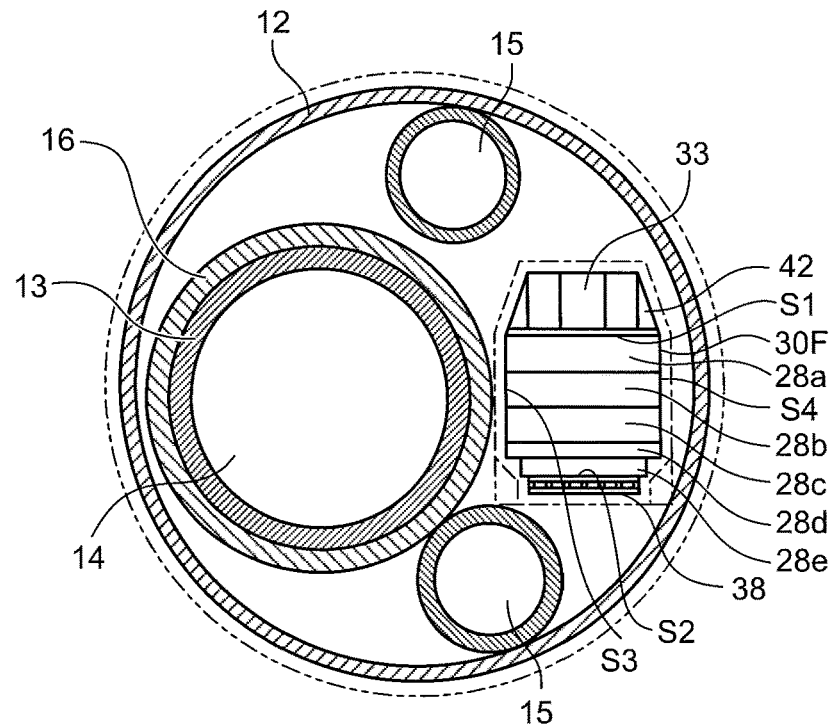
FIG. 17 is a cross-sectional view of a distal end of an endoscope according to a fourth embodiment of the present disclosure.

FIG. 17 is a cross-sectional view of a distal end of an endoscope according to a fourth embodiment of the present disclosure. The cross-sectional view illustrated in FIG. 17 is taken at the same position as the B-B line of FIG. 2. In FIG. 17, a maximum external shape of an imaging device according to the fourth embodiment is indicated by a one-dot chain line, and a maximum external shape of the conventional imaging device is indicated by a two-dot chain line, around a rigid circuit board 30F. In the endoscope according to the fourth embodiment, the rigid circuit board 30F includes a plurality of layered substrates 28a to 28e, and the substrate 28e connected to the flexible circuit board 38 has a width orthogonal to the longitudinal direction thereof, and formed smaller than those of the other substrates 28a to 28d. The other configuration is similar to that of the first embodiment.

The rigid circuit board 30F includes the layered substrates 28a, 28b, 28c, 28d, and 28e, and the substrates 28a to 28e are axially layered.

According to the fourth embodiment, the width of the substrate 28e orthogonal to the longitudinal direction is formed smaller than those of the other substrates 28a to 28d, and the width of the first surface S1 is larger than the width of the second surface S2, in a cross-section orthogonal to a longitudinal direction of the rigid circuit board 30F. Since the third surface S3 is adjacently opposed to the forceps channel 14, interference between the rigid circuit board 30F, the forceps channel 14, and the sheath tube 12 are not generated, and the distal end portion may have an outer diameter smaller than that of the conventional one.

Fifth Embodiment

Figure 18:
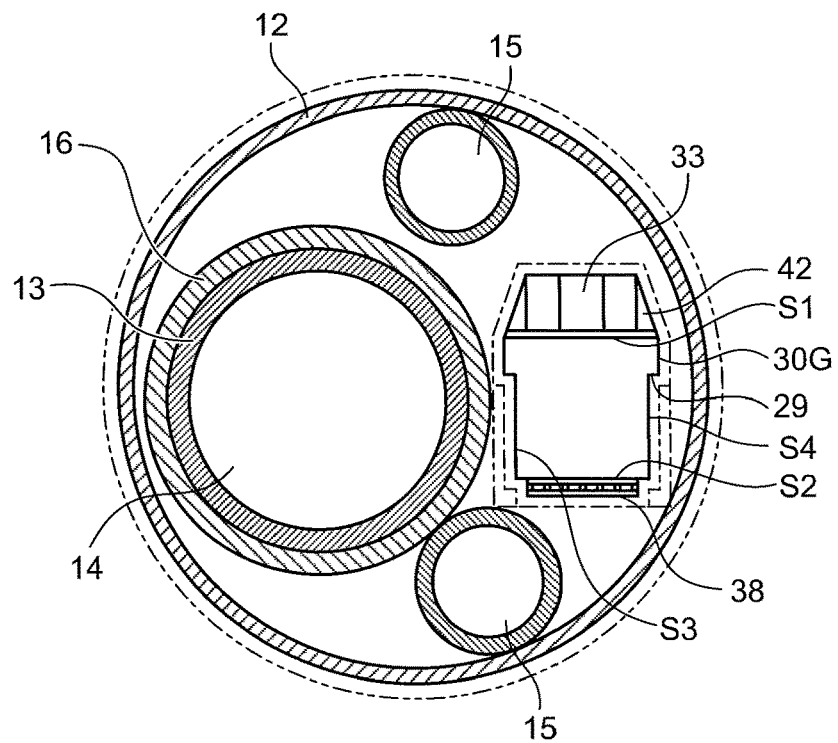
FIG. 18 is a cross-sectional view of a distal end of an endoscope according to a fifth embodiment of the present disclosure.
Figure 19:
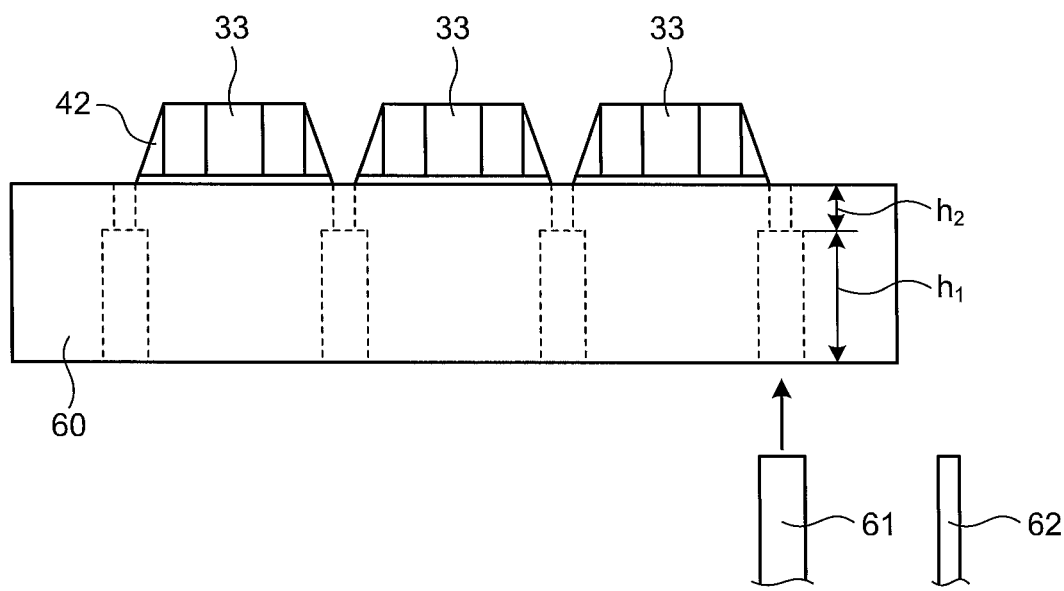
FIG. 19 is a diagram illustrating a manufacturing process of a rigid circuit board of FIG. 18.

FIG. 18 is a cross-sectional view of a distal end of an endoscope according to a fifth embodiment of the present disclosure. The cross-sectional view illustrated in FIG. 18 is taken at the same position as the B-B line of FIG. 2. In FIG. 18, a maximum external shape of an imaging device according to the fifth embodiment is indicated by a one-dot chain line, and a maximum external shape of the conventional imaging device is indicated by a two-dot chain line, around a rigid circuit board 30G. FIG. 19 is a diagram illustrating a manufacturing process of the rigid circuit board according to the fifth embodiment. In the endoscope according to the fifth embodiment, a step portion 29 is provided on the third surface S3 and the fourth surface S4 of the rigid circuit board 30G. The other configuration is similar to that of the first embodiment.

The step portion 29 of the rigid circuit board 30G may be manufactured such that the electronic component 33 and the like are mounted on a collective substrate 60, the collective substrate 60 is cut to a predetermined position, for example $h_1$ illustrated in FIG. 19, with a dicing blade 61 having a larger diameter, and then, remaining $h_2$ is cut with a dicing blade 62 having a small diameter. The step portion 29 may be a rounded portion (curved surface portion).

According to the fifth embodiment, the step portions 29 are provided on the third surface S3 and the fourth surface S4, and the width of the first surface S1 may be formed larger than the width of the second surface S2, in a cross-section orthogonal to a longitudinal direction of the rigid circuit board 30G. Since the third surface S3 is adjacently opposed to the forceps channel 14, interference between the rigid circuit board 30G, the forceps channel 14, and the sheath tube 12 are not generated, and the distal end portion may have a reduced outer diameter.

Sixth Embodiment

Figure 20:
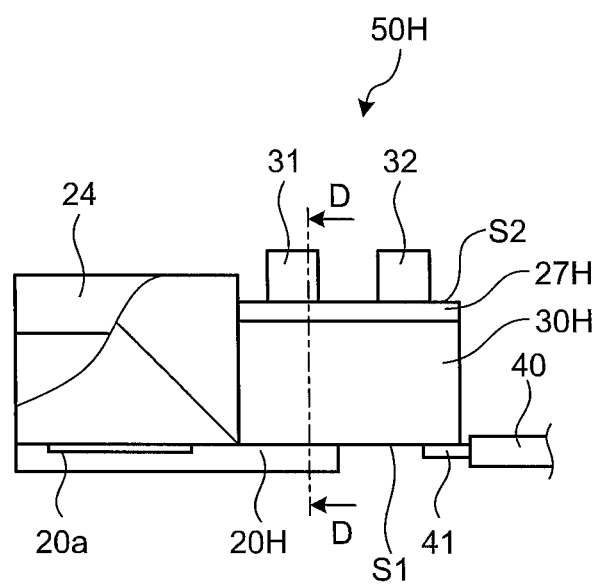
FIG. 20 is a side view of an imaging unit according to a sixth embodiment of the present disclosure.
Figure 21:
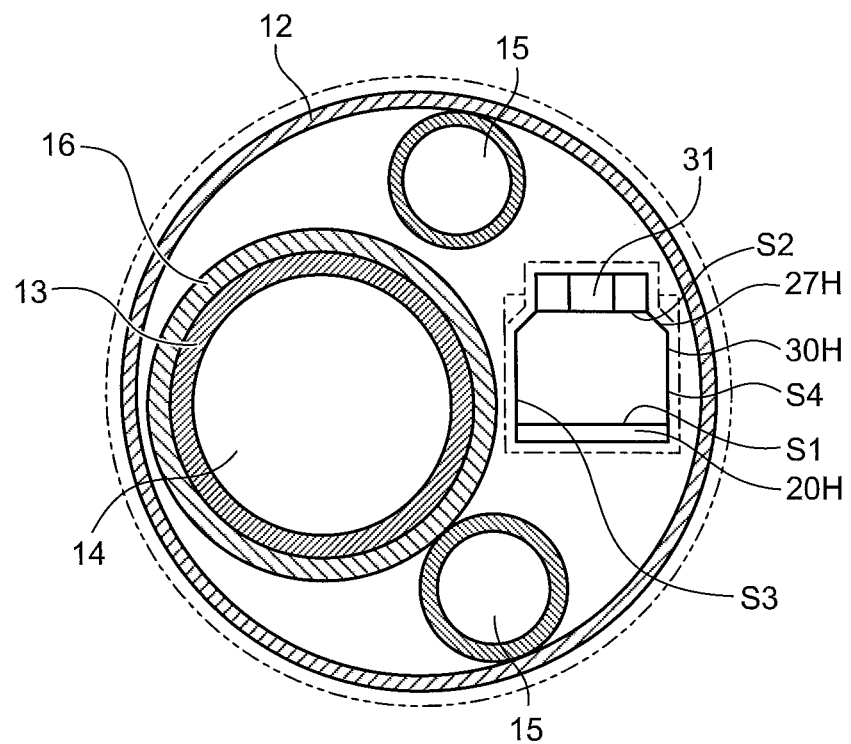
FIG. 21 is a cross-sectional view of a distal end of an endoscope using the imaging unit of FIG. 20.

FIG. 20 is a side view of an imaging unit according to a sixth embodiment of the present disclosure. FIG. 21 is a cross-sectional view of a distal end of an endoscope using the imaging unit of FIG. 20, and is a cross-sectional view of the distal end of the endoscope which is taken along a line D-D of FIG. 20. In FIG. 21, a maximum external shape of an imaging device according to the sixth embodiment is indicated by a one-dot chain line, and a maximum external shape of the conventional imaging device is indicated by a two-dot chain line, around a rigid circuit board 30H. In an imaging unit 50H according to the fifth embodiment, a solid state image sensor 20H has the light receiving unit 20a positioned parallel to the axial direction of the distal end portion of the endoscope, that is, the light receiving unit 20a is mounted laterally.

In the imaging unit 50H, a prism 24 reflects light emitted from the lens unit (not illustrated), and the light reflected from the prism 24 is received by the light receiving unit 20a. The solid state image sensor 20H is mounted laterally so that the light receiving unit 20a is positioned horizontally, and the prism 24 is bonded over the light receiving unit 20a. The solid state image sensor 20H has a proximal end to which the rigid circuit board 30H is connected. In the rigid circuit boards 30H, lands on the circuit board for connection with the solid state image sensor 20H is formed on the first surface S1, and the first surface S1 is disposed opposite to a light receiving surface of the solid state image sensor 20H. Note that the lands on the circuit board for connection with the solid state image sensor 20H may be formed on the second surface S2 of the rigid circuit board 30H so that the second surface S2 is opposed to the light receiving surface of the solid state image sensor 20H.

A chamfered portion 27H is provided on the third surface S3 and the fourth surface S4 of the rigid circuit board 30H according to the sixth embodiment. The chamfered portions 27H are formed at corners of the third surface S3 and the fourth surface S4 of the rigid circuit board 30H having a cuboid shape, similarly to the chamfered portion 27 of the third embodiment.

According to the sixth embodiment, the chamfered portions 27H are provided on the third surface S3 and the fourth surface S4, and the width of the first surface S1 may be formed larger than the width of the second surface S2, in a cross-section orthogonal to a longitudinal direction of the rigid circuit board 30H. Since the third surface S3 is adjacently opposed to the forceps channel 14, interference between the rigid circuit board 30H, the forceps channel 14, and the sheath tube 12 are not generated, and the distal end portion may have a reduced outer diameter.

According to the present disclosure, the endoscope which may achieve reduction in diameter of the insertion section may be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an imaging unit disposed at a distal end portion of an insertion section, the insertion section being configured to be inserted into a body of a subject; and
   a built-in component provided parallel with the imaging unit at the distal end portion, and extending substantially parallel with an axial direction of the insertion section, wherein
   the imaging unit includes:
   a solid state image sensor including a light receiving unit;
   a flexible circuit board electrically connected to the solid state image sensor; and
   a rigid circuit board at least partially disposed on a proximal end side of the endoscope relative to the solid state image sensor, and electrically connected to the flexible circuit board,
   the rigid circuit board includes a first surface whose longitudinal direction extends in an axial direction of the distal end portion, and a second surface opposed to the first surface substantially in parallel, the first surface having a width larger than a width of the second surface in a cross-section orthogonal to the longitudinal direction,
   the rigid circuit board includes a third surface and a fourth surface different from the first surface and the second surface, and the third surface and the fourth surface extending in an axial direction of the distal end portion, and the third surface or the fourth surface being opposed to the built-in component, the solid state image sensor includes a light receiving surface provided with the light receiving unit, a land on the sensor for connection with the flexible circuit board is formed on the light receiving surface, and the light receiving surface extends in a plane orthogonal to the axial direction of the distal end portion, the rigid circuit board is formed with a land on the circuit board for connection with the flexible circuit board, on the first or second surface, and is disposed such that a fifth surface orthogonal to the axial direction of the distal end portion is opposed to a surface of the solid state image sensor opposite to the light receiving surface of the solid state image sensor, and the flexible circuit board is disposed to be opposed to a side surface of the solid state image sensor, and the first or second surface of the rigid circuit board.

2. The endoscope according to claim 1, wherein
the built-in component comprises a plurality of the built-in components, the plurality of built-in components being stored in the insertion section, and
the third surface or the fourth surface is opposed to a built-in component having a largest diameter of the plurality of built-in components.

3. The endoscope according to claim 1, wherein a circuit pattern is arranged on each of the first surface and the second surface of the rigid circuit board, and at least one cable land is provided on a proximal end side of the first surface, the at least one cable land being configured to connect to a cable.

4. The endoscope according to claim 1, further comprising a plurality of electronic components mounted on the rigid circuit board, and an electronic component having a highest mounting height among the plurality of electronic components is mounted on the first surface.

* * * * *